United States Patent
Cussonneau et al.

(10) Patent No.: US 9,349,577 B2
(45) Date of Patent: May 24, 2016

(54) PROCESS FOR LOCATING A POSITRON RADIONUCLIDE, APPLICATIONS AND DEVICE FOR IMPLEMENTING SAME

(75) Inventors: Jean-Pierre Cussonneau, La Rebionnière (FR); Patrick Le Ray, Saint Herblain (FR); Eric Morteau, La Chaussaire (FR); Noël Servagent, La Chapelle sur Erdre (FR); Dominique Thers, Treillieres (FR)

(73) Assignees: CENTRE NATIONAL DE LA RECHERCHE SCIENTIFIQUE (CNRS), Paris (FR); ECOLE DES MINES DE NANTES, Nantes (FR)

(*) Notice: Subject to any disclaimer, the term of this patent is extended or adjusted under 35 U.S.C. 154(b) by 537 days.

(21) Appl. No.: 12/864,354
(22) PCT Filed: Jan. 23, 2009
(86) PCT No.: PCT/EP2009/050748
§ 371 (c)(1), (2), (4) Date: Jul. 23, 2010
(87) PCT Pub. No.: WO2009/092778
PCT Pub. Date: Jul. 30, 2009

(65) Prior Publication Data
US 2010/0294945 A1 Nov. 25, 2010

(30) Foreign Application Priority Data
Jan. 25, 2008 (FR) .................................. 08 50485

(51) Int. Cl.
*G01J 1/42* (2006.01)
*H01J 47/12* (2006.01)
(52) U.S. Cl.
CPC .................................. *H01J 47/1216* (2013.01)
(58) Field of Classification Search
USPC ............... 250/370.1, 363.01, 363.02, 363.03, 250/363.04
See application file for complete search history.

(56) References Cited

U.S. PATENT DOCUMENTS 4,833,327 A * 5/1989 Hart .......................... 250/363.01
5,821,541 A * 10/1998 Turner ..................... 250/370.09
(Continued)

OTHER PUBLICATIONS

Oberlack, U.G. et al.; "Compton Scattering Sequence Reconstruction Algorithm for the Liquid Xenon Gamma-Ray Imaging Telescope (LXeGRIT);" XP002504704, Online—URL:http://arXiv.org/PS_cache/astro-ph/pdf/0012/0012296v1.pdf, Dec. 13, 2000; pp. 1-10.

(Continued)

*Primary Examiner* — Daniel Hess
*Assistant Examiner* — David Tardif
(74) *Attorney, Agent, or Firm* — Blakely Sokoloff Taylor & Zafman LLP

(57) ABSTRACT

The present disclosure relates to a method for locating a radionuclide emitting positons and having a child core emitting a photon by de-excitation, that includes detecting a radionuclide response line using a positon-emitting tomography camera. According to the disclosure, for each of the arrangements ordered by pairs of first and second interactions of the Compton type detected by a Compton telescope, the method comprises determining the angle between the direction of the incident photon of the first interaction and the geometrical axis connecting the position of the first interaction with the position of the second interaction, determining the half-aperture cones of the angle in which the geometrical surface does not include an intersection with line, selecting at least one cone in which the geometrical surface includes an intersection with line, selecting the radionuclide position from said reconstructed intersection of the response line with the geometrical surface of the selected cone.

11 Claims, 2 Drawing Sheets

(56) References Cited

U.S. PATENT DOCUMENTS

| | | | |
|---|---|---|---|
| 5,861,627 A * | 1/1999 | Basko et al. | 250/363.04 |
| 6,220,371 B1 * | 4/2001 | Sharma et al. | 175/50 |
| 6,484,051 B1 | 11/2002 | Daniel | |
| 2004/0021088 A1 | 2/2004 | Thers et al. | |
| 2006/0138332 A1 * | 6/2006 | Bryman | 250/363.03 |

OTHER PUBLICATIONS

Moses, W. W.; "Time of Flight in PET Revisited;" IEEE Transations on Nuclear Science, vol. 50, No. 5, Oct. 2003; pp. 1325-1330.

Chang, Hsiang-Kuang et al.; "The Nuclear Compton Telescope (NCT): Scientific Goals and Expected Sensitivity;" ScienceDirect, Advances in Space Research 50, 2007; pp. 1281-1287.

Curioni, A. et al.; "A Study of the LXeGRIT Detection Efficiency for MeV Gamma-Rays During The 2000 Balloon Flight Campaign;" ScienceDirect, Nuclear Instruments & Methods in Physics Research A 576, 2007; pp. 350-361.

Kurfess, James D. et al.; "Abstract-Coincident Compton Nuclear Medical Imager;" XP002504705, 2001 IEEE Nuclear Science Symposium and Medical Imaging Conference Institute of Electrical and Electronics Engineers, Inc., vol. 2, Database Compendex, Database Accession No. E2002357064749, 2001; pp. 1166-1170.

Kurfess, James D. et al.; "Coincident Compton Nuclear Medical Imager;" 2001 IEEE Nuclear Science Symposium and Medical Imaging Conference Institute of Electrical and Electronics Engineers, Inc., 2001; pp. 1-5.

Grignon, C. et al.; "Abstrt-Nuclear Medical Imaging Using $/Beta+/ Gamma$ Coincidences From$^{\wedge}$ {4 Xenon As Detection Medium;" $1^{st}$ International Conference on Molecular Imaging Technology—EuroMedlm 2006, Marseille, France, 2007; 2 pages.

Grignon, C. et al.; "Nuclear Medical Imaging Using $\beta^{+}\gamma$ Coincidences From $^{44}$Sc Radio-Nuclide With Liquid Xenon As Detection Medium;" XP005737906, ScienceDirect, Nuclear Instruments & Methods in Physics Research A, vol. 571, No. 1-2, Jan. 26, 2007; pp. 142-145.

\* cited by examiner

PROCESS FOR LOCATING A POSITRON RADIONUCLIDE, APPLICATIONS AND DEVICE FOR IMPLEMENTING SAME

CROSS-REFERENCE TO RELATED APPLICATIONS

This application is a National Phase Entry of International Application No. PCT/EP2009/050748, filed on Jan. 23, 2009, which claims priority to French Application No. 0850485, filed on Jan. 25, 2008, both of which are incorporated by reference herein.

BACKGROUND AND SUMMARY

The present invention relates to a process for locating the position of a radionuclide emitting positrons during its disintegration and whereof the child core emits at least one photon by de-excitation.

A field of application is locating radioactive markers for example for therapeutic or other purposes, such as for example location of markers in a geological medium (underground, rocks) or on an in-depth sample in a geological medium (drillcores), for analysing the borrowed preferential trajectory in the flow of the radio element, such as for example for determining the flow sites of rainwater or waste water. Document [1] indicates that such a process can be executed by detecting by a positron emission tomography camera (PET in English) a response line of the radionuclide. According to document [1], the position of the radionuclide is situated at the intersection between the response line and a geometric cone determined from a Compton telescope, the cone having as apex the interaction position of Compton type detected in a detection medium of Compton interactions of the telescope from the photon emitted by the radionuclide, and for semi-opening the angle between the direction of the incident photon of the interaction and the axis of revolution of the cone formed by the direction joining this interaction and the position of another interaction detected by the telescope. Document [1] specifies that measuring the three coordinates and the energy of the two first interactions of the incident photon should be used, but omits describing how to identify these two first interactions via Compton telescope.

The aim of the invention is to provide a process for locating the radionuclide contributing means for resolving this problem. An object of the invention is a process for locating the position of a radionuclide emitting positrons and whereof the child core emits at least one photon by de-excitation, in which a response line of the radionuclide is detected by a positron emission tomography camera, the position of the radionuclide being situated at the intersection between the response line and a determined geometric cone, the cone having as apex the interaction position of Compton type from the photon emitted by the radionuclide, and as semi-opening the angle between the direction of the incident photon of the interaction and the axis of revolution of the cone formed by the direction joining this interaction and the position of another interaction, characterised in that a Compton telescope is used for detecting a plurality, greater than or equal to two, of interactions of Compton type caused in cascade in a detection medium of the Compton telescope from the photon emitted by the radionuclide, the position of each interaction of said plurality is measured by Compton telescope, for each of the multiplicity of arrangements ordered per pair of first and second interactions of Compton type among the plurality of interactions detected, the angle between the direction of the incident photon of the first interaction and the geometric axis joining the position of the first interaction and the position of the second interaction is determined by Compton telescope and the geometric surface of the cone having as apex the position of the first interaction and as semi-opening said angle determined around said geometric axis is reconstructed, said geometric axis forming the axis of revolution of the cone and being oriented in the direction going from the second interaction to the first interaction, those cones arc eliminated whereof the geometric surface has no intersection with the response line, at least one cone whereof the geometric surface has an intersection with the response line is selected, and the position of the radionuclide is selected from said reconstructed intersection of the response line with the geometric surface of the selected cone.

In accordance with embodiments of the invention:
said angle mn for each arrangement per pair is determined by Compton telescope according to the formula:

$$\cos \theta_{mn} = 1 + m_e c^2 (1/E_{0m} - 1/(E_{0m} - E_{1m}))$$

where $m_e$ is the mass of the electron, c represents the speed of light in vacuum, $E_{0m}$ is the measured energy of the incident photon of the first interaction of the pair, $E_{1m}$ is the energy transferred to an electron during the first interaction and measured.

it is determined whether there is only a single selected cone whereof the surface has a point of intersection with the response line, and, in the affirmative, the position of the radionuclide is calculated as being the position of this point of intersection of this single selected cone whereof the surface has a point of intersection with the response line.

it is determined whether there are several selected cones whereof the surface has a point of intersection with the response line, and, in the affirmative, it is determined which of these selected cones whereof the surface has a point of intersection with the response line is the most probable, the position of the radionuclide is calculated as being the position of the point of intersection of the selected cone whereof the surface has a point of intersection with the response line and which is the most probable.

Other objects of the invention are the following:
Application of the process such as described hereinabove to location imagery of the radionuclide.
Application of the process such as described hereinabove to locating at least one radioactive marker comprising said radionuclide.
This last application can serve to locate at least one radioactive marker, comprising the radionuclide, for locating a radiomarked substance by the marker in a geological medium.
In this last application the radiomarked substance can be water.
Application of the process such as described hereinabove to locating at least one radioactive marker, comprising the radionuclide, to mark a chemical substance in a human or animal body.
Application of the process such as described hereinabove to locating at least one radioactive marker, comprising the radionuclide, to mark a chemical substance in a human or animal body, having been introduced to said body.
Application of the process such as described hereinabove to detection of leaks from a container containing at least the radionuclide.

Application of the process such as described hereinabove to detection of an object containing at least the radionuclide.

Another object of the invention is a device for carrying out the process such as described hereinabove, comprising a positron emission tomography camera for detecting a response line of the radionuclide, a Compton telescope comprising:

means for detecting a plurality, greater than or equal to two, of interactions of Compton type caused in cascade in a detection medium of the Compton telescope from the photon emitted by the radionuclide, means for measuring the position of each interaction of said plurality in the detection medium, the device comprising, in addition to the camera and the telescope:

means for determining, for each of the multiplicity of arrangements ordered per pair of first and second interactions of Compton type among the plurality of interactions detected, the angle between the direction of the incident photon of the first interaction and the geometric axis joining the position of the first interaction and the position of the second interaction, to reconstruct the geometric surface of the cone having for apex the position of the first interaction and for semi-opening said angle determined around said geometric axis, said geometric axis forming the axis of revolution of the cone and being oriented in the direction going from the second interaction to the first interaction, means for eliminating the cones whereof the geometric surface has no intersection with the response line, means for selecting at least one cone whereof the geometric surface has an intersection with the response line, means for selecting the position of the radionuclide from said reconstructed intersection of the response line with the geometric surface of the selected cone.

BRIEF DESCRIPTION OF THE DRAWINGS

The invention will be better understood from the following description, given solely by way of non-limiting example in reference to the attached diagrams, in which.

DETAILED DESCRIPTION

In the following, the radionuclide R in question emits one or more positrons β+ and one or more first photons γ1. This radionuclide is for example $^{44}$Sc, but could also be $^{14}$O, $^{82}$Rb, $^{94}$Tc metastable, $^{44}$Sc metastable, $^{22}$Na, $^{48}$Va, $^{94}$Tc. The positron β+ interacts with the surrounding material to emit two second and third γ2 and γ3 photons in two directions D2 and D3, substantially at 180° to one another, the γ2 and γ3 photons each having energy of 511 keV. The two second and third γ2 and γ3 photons are detected by two first and second detectors 12 and 13 of the positron emission tomography camera PET 1 placed adequately. These detectors for example form part of a detection ring of γ2 and γ3 photons, as is known by the expert. During a first calculation step S1 the spatial position of impact points 14, 15 of the second and third γ2 and γ3 photons on the detectors 12 and 13 calculates the response line 16 (LOR) of the radionuclide, which is formed by the directions D2 and D3. A PET scanner is described for example in document [4].

Interactions caused by the first photon γ1 are detected by a Compton telescope 2. An example of a Compton telescope is described in document [3]. An example of a solid Compton telescope is described in document [5]. The Compton telescope is used to detect the photon emitted to coincide temporally and spatially with the positron detected in PET functional imagery. The camera PET locates the LOR site of the point of emission on a segment.

Figure 1:
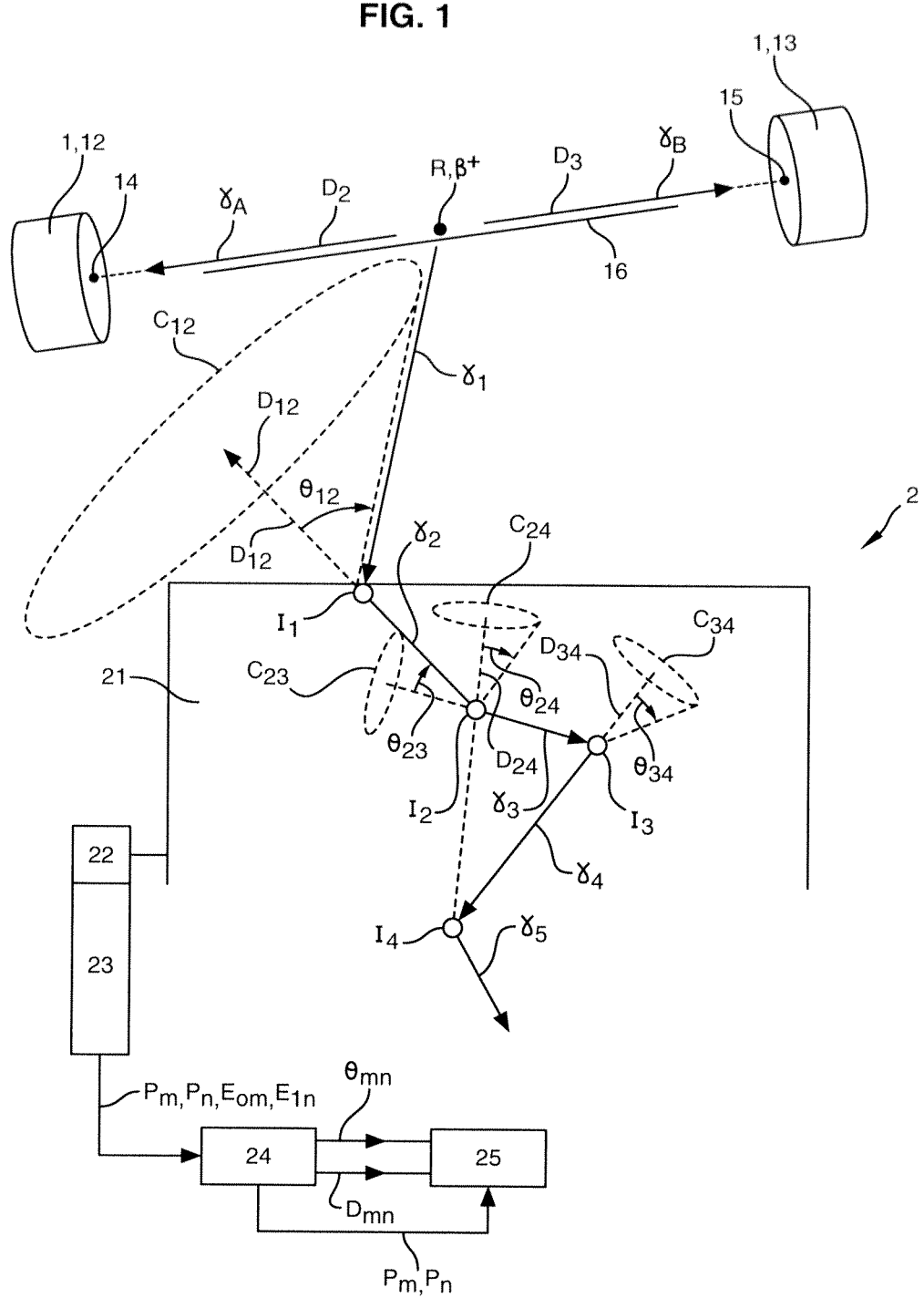
FIG. 1 is a sketch showing interactions caused by a disintegrating radionuclide, and a device for carrying out the process according to the invention.
Figure 2:
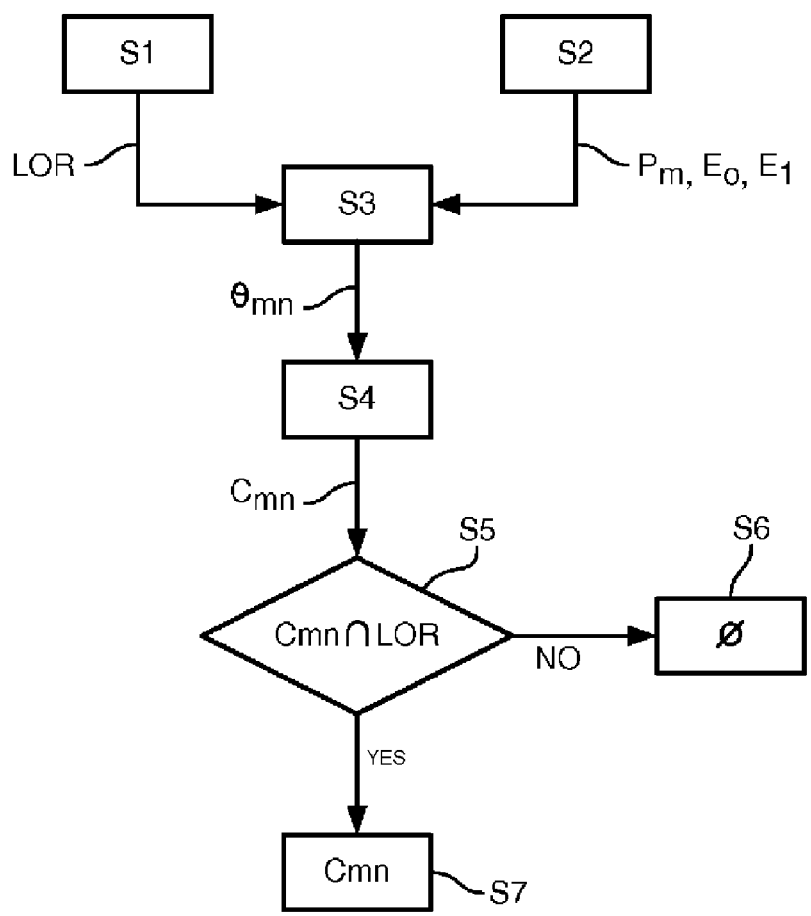
FIG. 2 is an organigram of steps carried out in the process according to the invention to reconstitute the Compton sequence caused by the radionuclide.

The Compton telescope 2 comprises a detection medium 21 of interactions of Compton type, formed for example by xenon kept in the liquid state. The first incident γ1 photon causes several Compton interactions in cascade in the detection medium 21. Each Compton interaction caused by an incident $γ_n$ photon causes emission of a fresh $γ_{n+}1$ photon and absorption of energy by an electron of the detection medium 21. This fresh photon in turn causes a new Compton interaction in the medium 21. By way of example FIG. 1 illustrates four successive Compton interactions I1, I2, I3, I4 in the medium 21 from the γ1 photon, and the associated emitted γ2, γ3, γ4, γ5 photons. The number of interactions is for example at least three. The interactions and the lines represented in FIG. 1 are not necessarily in the same plan of course, but are in three dimensions.

The Compton telescope 2 comprises means 22 for measuring the respective spatial position P1, P2, P3, P4 of the Compton interactions I1, I2, I3, I4 in the detection medium 21, each spatial position comprising the coordinates, for example Cartesian x, y, z of the interaction. The Compton telescope 2 comprises measuring means 23 for each detected interaction I1, I2, I3, I4, of:

the energy $E_0$ of the incident photon of the interaction,
the energy $E_1$ transferred to an electron of the detection medium 21.

The transferred energy $E_1$ causes displacement of electrons in the detection medium 21, which measures via means 23 an electric current used to calculate the value of the transferred energy $E_1$. In this way, means for collection of the current, amplification and processing thereof are provided. The positions Pm of the Compton interactions In and the energies $E_0$ and $E_1$ associated with each interaction In are determined by the Compton telescope during a step S2.

For each pair of interactions $1_m$, $I_n$ of those detected a calculation unit 24 calculates during a step S3 successive to steps S1 and S2 an associated angle mn according to the formula:

$$\cos \theta mn = 1 + m_e c^2 (1/E_{0m} - 1/(E_{0m} - E_{1m}))$$

where $m_e$ is the mass of the electron, c represents the speed of the light in vacuum, $E_{0m}$ is the measured energy of the incident photon of the first $1_m$ interaction of the pair, $E_{1m}$ is the energy transferred to an electron during the first $1_m$ interaction and measured, the angle $\theta_{mn}$ representing the angle between the direction of the incident photon of the first interaction $1_m$ and the axis $D_{mn}$ passing through the position Pm having been determined of the first I interaction and the position Pn having been determined of the second $I_n$ interaction of the pair. The axis $D_{mn}$ is oriented from the second $I_n$ interaction to the first $1_m$ interaction.

The radionuclide R is on the surface of the geometric cone C12, defined as follows in three dimension for the first interaction I1:

apex of the cone C12: position P1 of the interaction I1,
cone of revolution around the axis D12 passing through the determined position P1 of the interaction I1 and the position P2 of the second interaction I2, angle of semi-opening of the cone C12 relative to its axis D12 of revolution, equal to $\theta_{12}$, opening cone C12 directed in inverse direction of I2.

As per the invention, the process described hereinbelow is executed by calculation means 25. The different steps of the process are implemented automatically by a calculator. The surface of the geometric Cmn cone, defined as follows in three dimensions for the first interaction $I_m$, is determined during a step S4 after step S3, for each ordered pair of first interaction $1_m$ and second interaction $I_n$ of interactions of those detected I1, I2, I3, I4, I5:

apex of the Cmn cone: position Pm of the first interaction Im of the ordered pair, Cmn cone of revolution about the axis $D_{mn}$ passing through the position Pm determined from the first interaction $I_m$ of the ordered pair and the position Pn of the second interaction $I_n$ of the ordered pair, semi-opening angle of the Cmn cone relative to its axis $D_{mn}$ of revolution, equal to $\theta_{mn}$, opening Cmn cone directed in the inverse direction of the second In interaction of the ordered pair.

FIG. 1 illustrates only cones C12, C23, C34 and C24, the associated semi-opening angles $\theta_{12}$, $\theta_{23}$, $\theta_{34}$, $\theta_{24}$ and the associated axes D12, D23, D34, D24 of all possible arrangements. Of course, there are also all the other cones not shown to be considered, that is to say for four interactions, eight other cones. The number of arrangements per pair of interactions of the Q Compton interactions detected in the medium 21 is equal to $Q \cdot (Q-1)$. During a step S5 after step S4, each calculated Cmn cone is examined to see if its surface has an intersection with the response line LOR 16.

Those Cmn cones whereof the surface does not have a point of intersection with the response line LOR 16 in step S6 are rejected. The Cmn cone or those Cmn cones whereof the surface has a point of intersection with the response line LOR 16 in step S7 are selected. When there is only a single Cmn cone whereof the surface has a point of intersection with the response line LOR 16, the position of this point of intersection representing the position of the radionuclide R is calculated. The uniqueness of a Cmn cone occurs in more than two cases out of three.

When there are several Cmn cones whereof the surface has a point of intersection with the response line LOR 16, it is determined which of these selected Cmn cones is the most probable, for example by using the algorithm described by document [2]. The most probable cone for calculating the position of the point of intersection of the Cmn cone retained with the response line LOR 16 is kept, which then represents the position of the radionuclide R. The point of intersection determines the site of the radionuclide in three dimensions. It is a solution of the intersection of the cone and of the response segment LOR (equation of the second degree comprising only one physical solution in the field of view in 90 to 95% of cases, the 5 to 10% remaining are rejected to reconstruction). The process according to the invention multiplies the detection sensitivity of the camera PET and of the Compton telescope by more than two relative to the algorithm known from document [2].

Once the position of the radionuclide R is determined it can be exploited, for example by indicating this to the user by any appropriate indication means. For example, the position of the radionuclide R is indicated on an image. This position indication for example takes the form of one or more image pixels having an appearance recognisable for the user (for example level of grey, light intensity or colour), different to the environment where a radionuclide has not been detected. This results in an imagery process.

Fields of application of the invention are the following: pharmacology, clinical medical imagery, associated instrumentation. One application relates to radioactive marking of theracanic, diagnostic or other molecules in the human or animal body, for purposes of follow-up of same. The radionuclide can serve as radiotracer. In particular, a functional imagery process on the small animal can be obtained, for example for bioclinical evaluation of biomolecules (peptides, antibodies). Improved detection of radionuclides reduces the dose of radioactivity to be introduced, minimising the risks encountered by handlers, which in the case of extensive use are considerable and avoids biasing the result of some preclinical evaluations (follow-up on tumoral growth, for example) by irradiation of animals for which there is a known impact on cellular metabolism. The sensitivity of PET cameras "current small animals" is good, but not excellent and the doses necessary for good imagery are not totally negligible. The imagery process can be used for early diagnostics of cancer, to assist beta radio-immunotherapy and more generally to envisage a drastic reduction of exposure to radioactivity associated with functional imagery.

Access to emitting radio elements β+ such as technetium 94, Whereof the analog 99m is widely used in nuclear medicine, must improve resolution of the imagery. Access to rubidium 82, analog of thallium 201, or to fatty acids radiomarked by iodine 124 or technetium 94, should enable realisation of effective imagery in the field of cardiologic ischaemia. The development de novel approaches to imagery such as remodelling imagery of the tissular environment with inhibitors of radioactive metalloproteins, or targeting apoptosis paths also open up novel perspectives in these fields. Another field of application for positron emitters relates to cancerology and follow-up of cells in cellular therapy. In this field, the development of complex lipophils of radioactive metals (copper 64) must enable follow-up of cells from their injection to their migration to sites of interest, or from a few minutes to a few days.

Of these radio elements the majority of candidates most often cited in literature, iodine 124, yttrium 86, rubidium 82 etc., has high-energy photonic emissions in addition to β+ emission. These emissions are the source of degradation of the PET image, impose additional restrictions in terms of radioprotection and boost the potential long-term risk of repeated PET usage.

The design of a novel camera, based on detection of 3 photons, enables imagery without reconstruction with much lower quantities of radioactivity and shorter acquisition times than those normally used. In all these applications the imagery of 3 photons could be applied with the advantage of low doses for examinations to be undertaken much more often than in the past and with greater rapidity of acquisition. All β+ emitters do not simultaneously emit utilisable gamma energy radiation, but this is the case of some of them (technetium 94, scandium 44, oxygen 14, . . . ) which could be produced and substituted for the preceding for imagery applications with 3 photons. Liquid xenon has been recognised for a long time as being a particularly appropriate medium for detection of corpuscular particles (leptons, γ, hadrons, super-symmetrical particles).

LIST OF REFERENCES CITED

[1] Nuclear medical imaging using $\beta^+$ γ coincidences from $^{44}$Sc radionuclide with liquid xenon as detection medium, by C. Grignon, J. Barbet, M. Bardies, T. Carlier, J. F. Chatal, O. Couturier, J. P. Cussonneau, A. Faivre, L. Ferrer, S. Girault, T. Haruyama, P. The Ray, L. Luquin, S. Lupone, V. Metivier, E. Morteau, N. Servagent, D. Thers, Nuclear Instruments and Methods in Physics Research A 571 (2007), pages 142-145.

[2] Compton scattering sequence reconstruction algorithm for the liquid xenon gamma-ray imaging telescope (LXeGRIT), de U. G. Oberlack, E. Aprile, A. Curioni, V. Egorov, K. L. Giboni, Columbia Astrophysics Laboratory, Columbia University, New York, USA, arXiv:astro-ph/0012296v1, Dec. 13, 2000.

[3] A study of the LXeGRIT detection efficiency for MeV gamma-rays during the 2000 balloon flight campaign, by A. Curioni, E O. Aprile, T. Doke, K. L. Giboni, M. Kobayashi, U. G. Oberlack, Nuclear Instruments and Methods in Physics Research A 576 (2007), pages 350-361.

[4] Time of Flight in PET Revisited, de W. W. Moses, IEEE Transactions on Nuclear Science, Vol. 50, N[deg.] 5, October 2003, pages 1325-1330.

[5] The Nuclear Compton Telescope (NCT): Scientific goals and expected sensitivity, de Hsiang-Kuang Chang, Steven Boggs, Yuan-Hann Chang, for the NCT collaboration, Advances in Space Research 40 (2007), pages 1281-1287.

The invention claimed is:

1. A process for locating the position of a radionuclide emitting positrons emitting second and third photons having opposed direction along a response line and whereof a child core emits at least one first photon other than the response line by de-excitation, the process comprising detecting a response line of the second and third photons by a camera with tomography by positron emission, using a Compton telescope for detecting a plurality, greater than or equal to two, of interactions of Compton type caused in cascade in a detection medium of the Compton telescope from the first photon, which is emitted by de-excitation child core of the radionuclide and is other than the response line, measuring the position of each interaction of the plurality by the Compton telescope, for each of the multiplicity of the arrangements ordered per pair of first and second interactions of Compton type among the plurality of detected interactions, determining the angle between the direction of the incident photon of the first interaction and the geometric axis which joins the position of the first interaction and the position of the second interaction by the Compton telescope and reconstructing the geometric surface of the cone having for apex the position of the first interaction and for semi-opening the angle determined around the geometric axis, wherein the geometric axis forms the axis of revolution of the cone and is oriented in the direction going from the second interaction to the first interaction, eliminating those cones where the geometric surface has no intersection with the response line, selecting at least one cone where the geometric surface is secant by a point of intersection with the response line which has been detected by the camera with tomography by positron emission and is not included in the geometric surface of the cone; and selecting the position of the radionuclide from the point of intersection of the response line secant with the geometric surface of the selected cone.

2. The process as claimed in claim 1, further comprising determining said angle $\theta_{mn}$ by the Compton telescope for each arrangement per pair as per the formula:

$$\cos \theta_{mn} = 1 + m_e c^2 (1/E_{0m} - 1/(E_{0m} - E_{1m})),$$

where $m_e$ is the mass of the electron, c represents the speed of light in vacuum, $E_{0m}$ is the measured energy of the incident photon of the first interaction ($1m$) of the pair, $E_{1m}$ is the energy transferred to an electron during the first interaction ($1m$) and measured.

3. The process as claimed in claim 1, further comprising making an examination as to whether there is only a single cone selected whereof the surface is secant by a point of intersection with the response line, and, in the affirmative, calculating the position of the radionuclide (R) as being the position of this point of intersection of this single selected cone whereof the surface is secant by a point of intersection with the response line.

4. The process as claimed in claim 1, further comprising making an examination as to whether there are several selected cones whereof the surface is secant by a point of intersection with the response line, and, in the affirmative, determining which of these selected cones whereof the surface is secant by a point of intersection with the response line is the most probable, and calculating the position of the radionuclide as being the position of the point of intersection of the selected cone, whereof the surface is secant by a point of intersection with the response line and which is the most probable.

5. The process as claimed in claim 1, further comprising determining location imagery of the radionuclide.

6. The process as claimed in claim 1, further comprising locating at least one radioactive marker comprising the radionuclide.

7. The process as claimed in claim 1, further comprising locating the at least one radioactive marker, comprising the radionuclide, to locate a radiomarked substance by the marker in a geological medium.

8. The process as claimed in claim 7, wherein the radiomarked substance is water.

9. The process as claimed in claim 1, further comprising making detecting leaks from a container containing at least the radionuclide.

10. The process as claimed in claim 1, further comprising detecting an object containing at least the radionuclide.

11. A device for locating the position of a radionuclide emitting positrons emitting second and third photons having opposed direction along a response line wherein the child core emits at least one first photon other than the response line by de-excitation, and detecting a response line of the second and third photons by a camera with tomography by positron emission, said device comprising:

a positron emission tomography camera detecting a response line of the second and third photons;

a Compton telescope comprising:

(a) a detector detecting a plurality, greater than or equal to two, of interactions of Compton type caused in cascade in a detection medium of the Compton telescope from the first photon, which is emitted by de-excitation of the child core of the radionuclide and is other than the response line;

(b) means for measuring the position of each interaction of the plurality in the detection medium, (c) at least one calculator determining, for each of the multiplicity of arrangements ordered per pair of first and second interactions of Compton type among the plurality of interactions detected, the angle between the direction of the incident photon of the first interaction and the geometric axis joining the position of the first interaction and the position of the second interaction, for reconstructing the geometric surface of the cone having for apex the position of the first interaction and for semi-opening the angle determined around the geometric axis, the geometric axis forming the axis of revolution of the cone and being oriented in the direction going from the second interaction to the first interaction;

(d) the at least one calculator eliminating the cones whereof the geometric surface has no intersection with the response line;

(e) the at least one calculator selecting at least one cone whereof the geometric surface is secant by a point of intersection with the response line which has been detected by the positron emission tomography camera and is not included in the geometric surface of the cone; and (f) the at least one calculator selecting the position of the radionuclide from the reconstructed point of intersection of the response line secant with the geometric surface of the selected cone.

* * * * *